United States Patent [19]
Etzkorn et al.

[11] Patent Number: 6,166,263
[45] Date of Patent: *Dec. 26, 2000

[54] PROCESSES FOR THE MANUFACTURE OF ACROLEIN

[75] Inventors: William George Etzkorn, Hurricane; Jonathan Lester Brockwell; Mark Anderson Young, both of South Charleston; John Michael Maher; Barbara Knight Warren, both of Charleston, all of W. Va.

[73] Assignee: Union Carbide Chemicals & Plastics Technology Corporation, Danbury, Conn.

[ * ] Notice: This patent is subject to a terminal disclaimer.

[21] Appl. No.: 09/169,335

[22] Filed: Oct. 9, 1998

Related U.S. Application Data

[63] Continuation-in-part of application No. PCT/US97/05100, Mar. 27, 1997.

[51] Int. Cl.⁷ .................................................. C07C 45/32
[52] U.S. Cl. ........................................ 568/469.9; 568/470
[58] Field of Search .................................. 568/41, 469.9, 568/470

[56] References Cited

U.S. PATENT DOCUMENTS

| | | | |
|---|---|---|---|
| 2,626,282 | 10/1953 | Cunningham et al. | 260/601 |
| 4,999,452 | 3/1991 | Bunning et al. | 560/208 |
| 5,155,262 | 10/1992 | Etzkorn et al. | 562/532 |
| 5,183,936 | 2/1993 | Etzkorn et al. | 562/532 |
| 5,198,578 | 3/1993 | Etzkorn et al. | 562/532 |
| 5,243,082 | 9/1993 | Etzkorn et al. | 568/465 |
| 5,321,180 | 6/1994 | Davis | 585/431 |
| 5,352,837 | 10/1994 | Hsu et al. | 568/41 |
| 5,354,915 | 10/1994 | Reichle | 568/881 |
| 5,637,766 | 6/1997 | Hsu et al. | 562/512 |
| 5,696,282 | 12/1997 | Shaw et al. | 560/152 |

FOREIGN PATENT DOCUMENTS

| | | |
|---|---|---|
| 0117146 | 8/1984 | European Pat. Off. . |
| 9736848 | 10/1997 | WIPO . |

*Primary Examiner*—Sreeni Padmanabhan
*Attorney, Agent, or Firm*—W. K. Volles

[57] ABSTRACT

Processes are disclosed for the conversion of propylene to acrolein in the presence of propane. The processes utilize oxygen and recycle propane to the acrolein reactor. Process feeds can comprise, propane, propylene or mixtures thereof. The presence of propane in the propylene-to-acrolein reaction can enhance the efficiency of the processes.

5 Claims, 1 Drawing Sheet

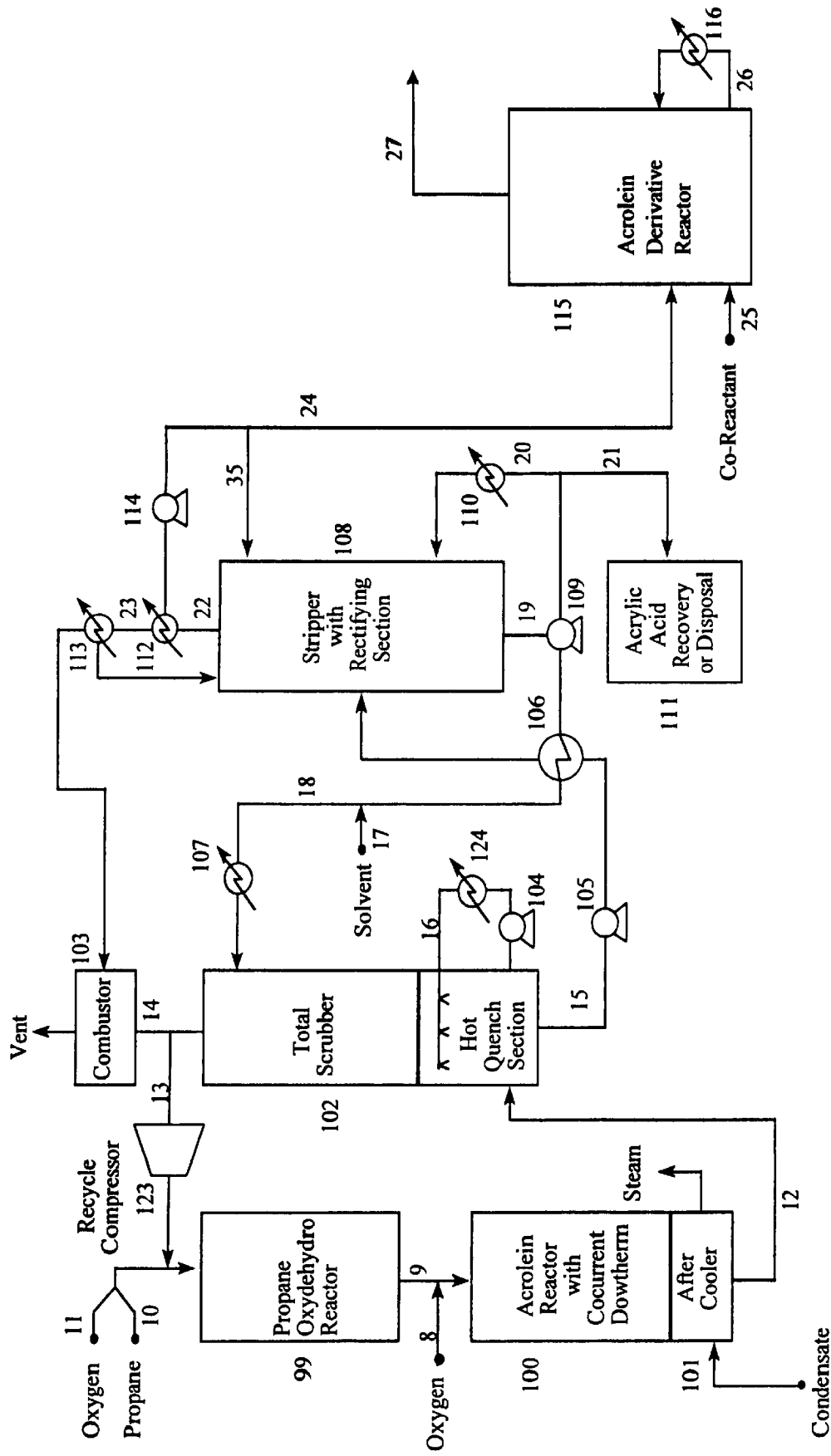
Figure 1: Acrolein Process

6,166,263

PROCESSES FOR THE MANUFACTURE OF ACROLEIN

CROSS-REFERENCE TO RELATED APPLICATION

This application is a continuation-in-part of PCT/US97/05100 filed Mar. 27, 1997.

FIELD OF THE INVENTION

This invention relates to the manufacture of acrolein by the conversion of propylene to acrolein in the presence of propane.

BACKGROUND OF THE INVENTION

Acrolein is a highly toxic and flammable material. It is conventionally produced by the vapor-phase oxidation of propylene over a solid-phase catalyst, producing a crude, gaseous reaction product which contains acrolein, water vapor, acrylic acid, acetaldehyde, and other organic by-products. Typically, the gas is treated to remove acrylic acid, then contacted with cooled water for absorption of the acrolein. The resultant aqueous solution is distilled to recover the absorbed acrolein and other organic components. The crude acrolein is then refined to reject lower-boiling impurities such as, for example, acetaldehyde, producing a purified, liquid acrolein product. Since the conventional processes typically use a batch reaction system, condensation and in-process storage of liquid acrolein is often necessary as a surge buffer between the acrolein production process and the process to produce derivatives of acrolein.

Storage of liquid acrolein involves significant toxicity, fire and explosion hazards. High capital and operating costs are consequently incurred in providing for the safe handling of acrolein. Substantial enhancements in the safety of handling acrolein would be achieved if acrolein were transferred directly and continuously from the acrolein manufacturing process to the acrolein derivative reaction zone without intermediate storage. Since the conventional, commercial processes for the preparation of acrolein derivatives, e.g., methylmercaptopropanal, also known in the art as 3-(methylthio)-propanal ("MMP") involve liquid-phase reactions, the need to condense the gaseous acrolein product has been considered unavoidable. However, further enhancements in the safety of handling acrolein and the process efficiency of manufacturing acrolein derivative could be achieved if the acrolein were transferred to the acrolein derivative reactor in the vapor phase, i.e., without significant condensation of the acrolein.

SUMMARY OF THE INVENTION

By the present invention, improved, continuous processes for the conversion of propylene to acrolein are provided via the production of acrolein in the presence of propane.

In one aspect of the present invention, the acrolein reaction is conducted in the presence of a recycle gas containing an effective amount of propane to enhance the efficiency of the acrolein reaction. Operation in this manner represents an improvement over the typical acrolein production processes in several ways. For example, the recycle process of the present invention can provide better distribution of the reaction load over the catalyst resulting in improved acrolein reaction efficiency and less by-product acrylic acid. In addition, in the present processes, oxygen rather than air, as is conventionally used, is fed to the acrolein reactor and unconverted propylene and oxygen are recycled to the acrolein reactor feed rather than purged and incinerated, which is necessary in an air-based process to avoid a build-up of nitrogen. The increased utilization of raw materials can substantially reduce operating expenses.

In another aspect of the invention, propane is used as the feed source. Existing processes for acrolein production typically use propylene as a feedstock for the production of acrolein. Propane is substantially cheaper than propylene, as well as being more widely available and more stable in price. In a preferred aspect of the present invention, oxydehydrogenation is used for the conversion of propane to propylene. This is particularly well-suited for integration of the propane conversion step and the acrolein derivative process. By operating at low propane conversions, the selectivity to propylene can be made quite high, e.g., between 80 and 100 mole percent. Since the feed to the acrolein reactor need only contain propylene in low concentration, e.g., 5 to 40 mole percent, the low conversion/high selectivity mode of operation can be highly efficient provided unreacted propane is recycled to the oxydehydrogenation reactor. Such recycle operation is feasible because typical oxydehydrocatalysts are unaffected by species such as carbon oxides and water which are formed in the acrolein reactor. Hence, after recovery of the acrolein, the noncondensable gas stream may be recycled without expensive purification steps.

BRIEF DESCRIPTION OF THE DRAWINGS

FIG. 1 is a simplified process flow diagram of a process for converting propane to acrolein and converting acrolein to an acrolein derivative in accordance with the present invention.

DETAILED DESCRIPTION OF THE INVENTION

Propylene-containing feed streams suitable for use in the processes of the present invention can be obtained from common chemical sources known to those skilled in the art. For example, the propane-containing propylene which is obtained in the dehydrogenation of propane by thermal cracking or catalyzed dehydrogenation can be used as the feedstream. Such feed streams typically comprise at least 50 mole percent, preferably at least 90 mole percent, and more preferably at least 95 mole percent propylene. Such feed streams also typically contain propane and other light hydrocarbons.

When propane feed is used in the process of the present invention, the source of the propane is not critical. The purity of the starting material propane is not particularly limited, and a propane feed containing a lower alkane such as methane or ethane, air or carbon dioxide, as impurities, may be used. Typically, the feed will comprise at least 30 mole percent, preferably at least 50 mole percent and more preferably at least 80 mole percent propane.

The oxygen source for use in the processes of the present invention (both for propane oxidation and propylene oxidation) is not critical. However, the use of air is not preferred because the nitrogen content can adversely affect the ability to recycle effluent gases. Preferably, the oxygen source comprises at least 90 mole percent and more preferably at least 95 mole percent oxygen. The ratio of propane to oxygen varies with the desired conversion and the selectivity of the catalyst, but generally is in the range of 2/1–40/1. The reaction can also be conducted in the presence of diluents such as, for example, steam. Such diluents, when employed, can be fed at 0–50 times the partial pressure of the propane, with 0.2–10 times being usual.

In the propane-to-propylene reaction, it is preferred to employ a starting material gas which contains steam. In such a case, as a starting material gas to be supplied to the propane reactor, a gas mixture comprising steam-containing propane and an oxygen-containing gas, is usually used. However, the steam-containing propane and the oxygen-containing gas may be alternately supplied to the reaction system. The steam to be employed may be present in the form of steam gas in the reaction system, and the manner of its introduction is not particularly limited. However, steam is not essential in the process of the present invention.

Any catalyst effective for the conversion of propane to propylene is suitable for use in the present invention. Preferred catalysts include, for example, oxydehydrogenation catalysts which comprise promoted MoVNb oxides, vanadyl pyrophosphate and other oxydehydrogenation catalysts. Such catalysts and others suitable for the oxidation of propane are described, for example, in U.S. Pat Nos. 4,148,757, 4,212,766, 4,260,822 and 5,198,580 and by E. M. Thorsteinson, T. P. Wilson, F. G. Young, and P. H. Kasai, J. Catal., 52, 116 (1978).

An example of a suitable catalyst for use in accordance with the present invention is a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium, wherein the proportions of the respective essential components, based on the total amount of the essential components exclusive of oxygen, satisfy the following formulas:

$$0.25 < r\ Mo < 0.98$$

$$0.003 < r\ V < 0.5$$

$$0.003 < r\ Te < 0.5$$

$$0.003 < r\ X < 0.5$$

wherein r Mo , r V, r Te and r X are molar fractions of Mo, V, Te and X, respectively, based on the total amount of the essential components exclusive of oxygen. This catalyst is further described in U.S. Pat. No. 5,380,933.

For the propane oxidation, the reaction temperature is usually from about 200 to 550° C., preferably from about 250 to 450° C., more preferably from about 350 to 440° C. The gas hourly space velocity in the vapor-phase reaction is usually within a range of from about 100 to 10,000 $hr^{-1}$, preferably from about 300 to 6,000 $hr^{-1}$, more preferably from about 300 to 2,000 $hr^{-1}$. As used herein, "gas hourly space velocity" means the volume of reactant gas at standard conditions (0° C. and 1 atmosphere ("atm") pressure) passed over the catalyst in one hour divided by the total volume occupied by the catalyst. Further, as a diluting gas to adjust the space velocity and the oxygen partial pressure, an inert gas such as nitrogen, argon or helium may be employed. This reaction is typically conducted at a slightly elevated pressure, e.g., 2 to 6 atm.

Any suitable reactor sequence known to those skilled in the art may be used for the propane-to-propylene reaction. For example, the reaction can be conducted in a single stage, or can be conducted in two or more stages with oxygen introduction between the stages where introduction of the entire oxygen requirement at a single point could create flammable process mixtures. Further details on the conversion of propane to propylene and suitable equipment, e.g., reactors, are known to those skilled in the art.

In the propane oxydehydrogenation reaction the propylene selectivity decreases with increasing propane conversion. Preferably, the propane-to-propylene reaction is conducted to provide for relatively low conversions of propane with high selectivities to propylene. More specifically, it is preferred that the conversion of propane be from about 5 to 40 percent and more preferably from about 10 to 30 percent. As used herein, the term "propane conversion" means the percentage of propane fed which is reacted. It is preferred that the selectivity of the conversion of propane to propylene be from about 50 to 98 percent and more preferably from about 80 to 98 percent. As used herein, the term "propylene selectivity" means the moles of propylene produced per mole of propane reacted expressed as a percentage.

In the present invention, propylene and oxygen are reacted over a catalyst at elevated temperature to produce acrolein. Water is a co-product of the reaction. A number of by-products are formed including carbon monoxide, carbon dioxide, formaldehyde, acetaldehyde, acetic acid and acrylic acid. Neither the propylene nor the oxygen in the reactor feed is totally converted. The noncondensable components in the reaction product, e.g., oxygen, propylene, carbon monoxide, carbon dioxide, propane and other light hydrocarbons, are separated from the condensable organic compounds, compressed and preferably recycled to the reactor inlet. In this way, utilization of oxygen and propylene can be very high.

In the aspect of the invention where the acrolein is passed to the acrolein derivative reactor in the vapor phase, the propylene-to-acrolein reaction is preferably conducted in the presence of an essentially anhydrous diluent gas such as described in U.S. Pat No. 5,198,578. The essentially anhydrous diluent gas typically comprises a mixture of nitrogen, carbon dioxide, methane, ethane and propane; however, any other essentially anhydrous inert gas can be included. Some other useful inert gases include helium, argon, hydrogen, saturated hydrocarbon gases, $N_2O$, and carbon monoxide. When water is present as a trace impurity in the feed introduced into the reactors, it is immediately converted to steam at the elevated temperature required for these reactions.

In other aspects of the present invention, some steam, e.g., about 0.3 to 8 moles per moles of propylene, may be utilized in the propylene-to-acrolein reaction. In these aspects, the steam may be effective in promoting the process possibly because it facilitates the desorption of the main products of the catalytic vapor-phase oxidation of propylene, i.e., acrolein and acrylic acid, or possibly because it participates directly in the reaction.

The propylene-to-acrolein reaction is not dependent upon any particular catalyst and any catalysts effective for the conversion of propylene to acrolein may be used. Typical catalysts are molybdenum-bismuth-iron-based mixed-metal-oxide oxidation catalysts, such as, for example, those disclosed in U.S. Pat. Nos. 3,825,600, 3,649,930, 4,339,355, 5,077,434 or 5,218,146. It may also be possible to conduct both the propane-to-propylene and propylene-to-acrolein reactions in a single reactor with one or more stages.

An example of a catalyst suitable for the propylene-to-acrolein reaction is an oxide catalyst containing Mo, Fe, and Bi. This catalyst is represented by the following general formula:

$$Mo_a\ W_b\ Bi_c\ Fe_d\ A_e\ B_f\ C_g\ D_h\ O_x$$

wherein Mo is molybdenum, Bi is bismuth, W is tungsten, Fe is iron, O is oxygen, A is at least one element selected from the group consisting of nickel and cobalt, B is at least one element selected from the group consisting of alkali metals, alkaline earth metals, and thallium, C is at least one element selected from the group consisting of phosphorus, arsenic, boron, and niobium, and D is at least one element selected from the group consisting of silicon, aluminum, and titanium, and the subscripts a, b, c, d, e, f, g, h, and x are respectively the numbers of atoms of the elements Mo, W, Bi, Fe, A, B, C, D, and O, providing that a=2 to 10, b=0 to 10, on condition that a+b=12, c=0.1 to 10.0 d=0.1 to 10, e=2 to 20, f=0.005 to 3.0, g=0 to 4, h=0.5 to 15, and x is a number required to satisfy the valance requirements of the other elements. This catalyst is described in U.S. Pat No. 5,218,146.

The catalysts for use in the processes of the present invention may be in the form of pellets, beads, or rings containing a through hole which are produced by a tableting machine or an extruding machine or otherwise in a form having catalytic components deposited on a refractory carrier. Suitable propylene-to-acrolein catalysts are commercially available, for example, from Nippon Shokubai, Tokyo, Japan; Nippon Kayaku, Tokyo, Japan; and Mitsubishi, Tokyo, Japan.

As regards typical acrolein reaction gas compositions, the content of propylene is in the range of 5 to 30 volume percent, preferably 7 to 15 volume percent, that of oxygen in the range of 8 to 40 volume percent, preferably 12 to 30 volume percent, that of a saturated aliphatic hydrocarbon having 1 to 5 carbon atoms, preferably 1 to 3 carbon atoms, e.g., propane, in the range of 5 to 80 volume percent, preferably 10 to 60 volume percent, that of carbon monoxide in the range of 0 to 50 volume percent, preferably 15 to 45 volume percent, that of carbon dioxide in the range of 0 to 50 volume percent, preferably 5 to 40 volume percent, (providing that the total content of the hydrocarbon, carbon monoxide and carbon dioxide is in the range of 40 to 90 volume percent, preferably 60 to 85 volume percent), and that of steam, when present, in the range of 0 to 50 volume percent, preferably 5 to 40 volume percent, (providing that the molar ratio of steam to propylene is in the range of 0.3 to 8, preferably 0.3 to 5), the molar ratio of oxygen to propylene is in the range of 1.0 to 2.5, preferably 1.5 to 2.0, and the contact time is in the range of 0.3 to 1.5 seconds, preferably 0.5 to 1.2 seconds. The catalyst is preferably capable of effecting a conversion of propylene of not less than 70 mole percent, preferably not less than 80 mole percent.

Preferably, the concentration of propane in the feedstream to the acrolein reaction zone is from about 5 to 70 volume percent, more preferably from about 10 to 60 volume percent and most preferably from about 10 to 40 volume percent, based on the total volume of the feedstream. As used herein, the terms "mole percent" and "volume percent" are equivalent as they relate to the concentrations of components in vapor streams.

Quite surprisingly, it has been found that the propylene-to-acrolein reaction efficiency can be substantially enhanced when using propane-containing feedstreams as described above. Preferably, the acrolein reaction efficiency is from about 65 to 97 percent and more preferably from about 75 to 90 percent. As used herein, the term "propylene-to-acrolein reaction efficiency" means moles acrolein produced per mole propylene fed expressed as a percentage.

Typically, approximate ranges for feed compositions are defined based on the generalized operating constraints discussed above. Propylene-to-acrolein reaction feeds in the following quantities are typically particularly useful:

Propylene: Up to about 16 g-mole per hour/liter of acrolein reaction catalyst, preferably up to about 10 g-mole per hour/liter of acrolein reaction catalyst;

Oxygen: 1.1 to 2.1:1 $O_2/C_3H_6$ ratio, such that there is up to about 33.6 g-mole per hour $O_2$/liter of acrolein reaction catalyst, preferably up to about 21 g-mole per hour $O_2$/liter of acrolein reaction catalyst;

Diluent: About 0.7 to 16:1 inert diluent/$C_3H_6$ ratio, preferably 2 to 10:1 inert diluent/$C_3H_6$ ratio.

The general reaction conditions are not narrowly critical, and are those known to the art. The propylene-to-acrolein reaction operates at temperatures of about 250 to 450° C., although temperatures of about 270 to 425° C. are preferred.

Operating pressures of about 1 to 4 atm. are typical, although subatmospheric, atmospheric, or superatmospheric pressures may be used. Preferred commercial modes of operation will often minimize pressures, but pressures are typically held in the 2-to 3-atm. range due to system pressure-drop constraints.

Flow rates can be varied to achieve contact times of from about 0.2 to 2 seconds in the propylene-to-acrolein reaction; however, typical commercial flows provide about 0.3 to 1.5 seconds contact time. Contact times of about 0.5 to 1.2 seconds are preferred. As used herein, "contact time" is defined as the ratio of the open volume in the catalyst bed to the process volumetric flow at process conditions.

The type of reactor used in the conversion of propylene to acrolein is not critical and may be, for example, a fixed-bed, tubular-flow reactor with liquid coolant passed through the shell. Fluidized bed reactors may also be employed. Further details of suitable reactors are known to those skilled in the art.

In accordance with the present invention, it is not necessary to highly purify the acrolein product prior to passing it to the acrolein derivative reactor. Also, it is not necessary to remove acetaldehyde from the acrolein product. Instead, the acetaldehyde can be removed from the acrolein derivative reaction product. As a result, the acetaldehyde removal can be conducted in a small distillation column, e.g., 3 theoretical trays, versus a much larger column when the acetaldehyde is removed from the acrolein product, e.g., 40 theoretical trays. Accordingly, the acrolein product may only need to be subjected to mild scrubbing and fractionation prior to being passed to the acrolein derivative reactor. If water is used as a scrubbing solvent, sufficient water must be removed in the fractionation step to avoid forming a two-phase liquid acrolein product.

Often, the acrolein produced by the process of the present invention is used on as an intermediate in the manufacture of an acrolein derivative. Typically, the acrolein product stream to be fed to the acrolein derivative reaction zone will comprise from about 0.5 to 3.5 weight percent, and preferably from about 1.0 to 2.5 weight percent acetaldehyde, from about 88 to 97 weight percent, preferably from about 93 to 97 weight percent acrolein, and from about 2 to 8 weight percent, preferably from about 2 to 4 weight percent water, based on the total weight of the acrolein product stream.

The particular acrolein derivative produced by the processes of the present invention is not critical. More specifically, the co-reactant reacted with the acrolein can be any compound capable of reacting with acrolein to form a desired product.

Often, the co-reactant is capable of undergoing a Diels-Alder reaction or a Michael Addition reaction, the details of which are known to be those skilled in the art. See, for example, J. March, "Advanced Organic Chemistry, 3rd Edition, page 745–758, (1985) and H. O. House, "Modern Synthetic Reactions", 2nd Edition, page 595–623, (1972). Typical of such co-reactants are the selected from the group consisting of butadiene, butadiene derivatives, vinyl ethers, alcohols and water.

In one aspect of the invention, the butadiene or butadiene derivative is selected from the group consisting of butadiene, methyl-pentadiene, myrcene and myrcenol. In this aspect of the invention, acrolein is a dieneophile, the butadiene or butadiene derivative is a diene and the acrolein derivative is a cyclohexene-carboxaldehyde or a cyclohexene-carboxaldehyde derivative.

In another aspect of the invention, the co-reactant is a vinyl ether, e.g., methyl vinyl ether, wherein acrolein is a heterodiene, the vinyl ether is a heterodienophile and the acrolein derivative is a 2-alkoxy-3,4-dihydro-2H-pyran, e.g., 2-methoxy-3,4-dihydro-2H-pyran. In a preferred aspect of the invention, the 2-methoxy-3,4-dihydro-2H-pyran is hydrolyzed in the presence of a suitable catalyst to produce glutaraldehyde.

In another aspect of the invention, the co-reactant is an alcohol which reacts with a carbon-carbon double bond of acrolein and/or a carbon-oxygen double bond on acrolein and the acrolein derivative is an alkoxypropionaldehyde, and acrolein acetal, or a 1,1,3-trialkoxypropane. Typical alcohols are selected from the group consisting of methanol, ethanol, ethylene, glycol, propylene glycol, 1,2,3 - propanetriol, pentaerythritol and allyl alcohol.

In another aspect of the invention, the co-reactant is water and the acrolein derivative is 3-hydroxypropionaldehyde which, for example, can by hydrogenated to produce 1,3-propane diol.

In another aspect of the present invention, the co-reactant is a mercaptan, which reacts with a carbon-carbon double bond of acrolein and the acrolein derivative is a mercaptopropionaldehyde.

In addition to the aspects of the invention described above, those skilled in the art will recognize that other co-reactants can be used to produce desired acrolein derivatives, such as, for example: ammonia to produce pyridine and beta-picoline; organic acids, e.g. acetic acid, propionic acid or benzoic acid, to produce an ester of beta-hydroxypropionaldehyde; organic anhydrides, e.g., acetic anhydride, to produce a 1,1-diacyloxy-2-propene; acrolein to react with itself to produce acrolein dimers and acrolein-based oligomers and polymers, and alcohols, e.g., isopropanol, to produce 3-isopropoxypropionaldehyde.

One preferred reaction is the reaction of methyl mercaptan ("MeSH") with acrolein to produce MMP. The acrolein-to-MMP reaction may be carried out, for example, at a temperature between about 30 and 80° C., preferably between about 40 and 70° C., for liquid-phase operation, and at a temperature of from about 80 to 400° C., preferably from about 150 to 300° C. and more preferably from about 180 to 260° C. for vapor-phase operation. The pressure is not critical and is typically between about 2 and 4 atmospheres. Methyl mercaptan and acrolein are preferably introduced into the reactor in a mercaptan-to-acrolein molar ratio of between about 0.95 and 1.2, but most preferably between about 1.00 and 1.02. Methyl mercaptan can be readily commercially obtained.

By establishing a very slight excess of mercaptan in the reactant mixture, conversion of acrolein is maximized and the need for disposition of unreacted acrolein is essentially obviated. Where the molar ratio of reactants is controlled in the range of between about 1.00 and 1.02 moles methyl mercaptan per mole of acrolein, direct reaction between the mercaptan and acrolein is effected in preference to formation of by-products. As a consequence, a high rate of reaction is realized, with high productivity and relatively low capital and operating expense of the reactor. The reactant ratio may be controlled by various means known in the art.

Conventional catalysts and catalyst concentrations may be used for the reaction. Such catalysts include a wide variety of organic amines such as, for example, pyridine, hexamethyltetraamine, or triethylamine. Organic acids are typically included to inhibit polymerization of acrolein. Where, for example, a pyridinium acetate catalyst is used, the concentration is maintained at between about 0.2 and 1.0 weight percent, preferably between about 0.35 and 0.5 weight percent by continuous or periodic additions of catalyst to the reaction medium.

The vapor-phase reaction can also be run without a catalyst. Preferably, the MMP reaction is conducted with at least 10 weight percent of the MMP in the vapor phase, preferably with at least 20 weight percent of the MMP in the vapor phase, more preferably with at least 50 weight percent of the MMP in the vapor phase, and most preferably with at least 80 weight percent of the MMP in the vapor phase, based on the total weight of MMP in the MMP reactor.

Any reactor suitable for the conversion of acrolein to MMP may be employed in the process of the present invention. Such reactors include, for example, liquid/gas contacting reactors such as described in U.S. Pat. No. 5,352,837, tubular plug-flow reactors, continuous stirred tank reactors, and other back-mixed reactors. Various combinations of two or more reactors may also be used to good advantage. Either a plug-flow reactor with high recycle or a continuous stirred tank reactor followed by a plug-flow reactor is preferred. Further details of suitable reactors are known to those skilled in the art.

The MMP product obtained from the process of the present invention, after purification and recovery known to those skilled in the art, may be used, for example, for the production of methionine and other compounds such as described in U.S. Pat No. 5,386,056.

The invention is hereafter described with reference to FIG. 1 which is not intended to limit the scope of the claims that follow.

With reference to FIG. 1, a feed containing about 90 volume percent propane in stream 10 is combined with oxygen in stream 11 and with compressed recycle gas in stream 13 at a pressure of about 30 to 90 psia and are fed to a reactor 99 containing a heterogeneous oxidative dehydrogenation catalyst (such as one of the preferred catalysts described above). The oxygen feed may be pure, or an air feed may be used. Recycle stream 13 is also fed to reactor 99. Stream 13 contains unconverted propane and oxygen which passed through the process without conversion at an earlier time. Stream 13 also contains propylene and water and various noncondensable gases which are not reactive in the process. Nonreactive gases would include, but not be limited to, carbon dioxide and carbon monoxide, and for the air-based process, nitrogen. All feed streams are preheated to approximately the operating temperature of reactor 99, which operates at no greater than 500° C. The pressure of the feed streams is slightly greater than the reactor pressure, which is between 30 and 90 psia. The gaseous species and the solid catalyst are contacted effectively in the reactor, which may have various designs including fixed or fluidized catalyst beds. The propane conversion to propylene is in the range of 5 to 40 percent. The gas product stream 9 contains the propylene product, unreacted propane and oxygen, water, small amounts of by-products, and the nonreactive feed species.

The crude propylene product stream 9 is passed directly, without purification, to the propylene oxidation reactor 100 where the contained propylene is oxidized to acrolein and/or acrylic acid. Additional oxygen is fed to reactor 100 in stream 8. Reactor 100 contains a heterogeneous catalyst for the oxidation of propylene (such as one of the preferred catalysts described above). The gaseous reactant and solid catalyst are contacted effectively in the reactor, which may have various designs including fixed or fluidized catalyst beds. Reactor 100 operates in the temperature range of 300 to 425° C. and a pressure range of 25 to 85 psia. The conversion of the contained propylene is approximately 90 percent, but may be in the range of 70 to 100 percent. The principal product is acrolein with acrylic acid being a minor co-product. The effluent stream 12 is immediately cooled to approximately 250° C. in aftercooler 101. Stream 12 has a pressure of approximately 20 psia, but it can range from 15 to 50 psia.

A wide variety of recovery and refining schemes may be employed to separate acrolein from effluent stream 12. One attractive scheme is presented in FIG. 1 for illustration, although numerous other effective schemes may be possible. Upon entering scrubber 102, stream 12 is cooled further via direct contacting with a liquid quench stream before passing into the scrubber section. The scrubbing liquid may be water, as used in current practice, or it may be any suitable solvent having a substantial capacity for absorbing acrolein. The condensable species, which are primarily acrolein, acrylic acid and water, are condensed by and mix with the scrubbing solvent. The remaining noncondensable species vent from the top of scrubber 102. Most of the vented material is recycled to the feed of reactor 100 in stream 13, after passing through compressor 123. A small purge stream 14 is routed to combustor 103 and subsequently vented from the process. Upon leaving the scrubber, the liquid solvent stream 15 has a temperature and pressure of approximately 50° C. and 20 psia, although these values may vary over a considerable range in order to optimize the process for a particular solvent. The temperature of stream 15 increases after it is pumped through heat exchanger and picks up heat from stream 18. The magnitude of the temperature increase depends largely upon the physical properties of the specific solvent used.

Stream 15 is fed to stripper/rectifier 108 above a section of stripping trays and below a section of rectification trays. Vapor created in heat exchanger 110 in the column bottom strips the acrolein product from the solvent in the stripping section. By contrast, the heavier acrylic acid concentrates in the liquid-solvent phase. The bottoms stream 19 is divided into three streams, i.e., 18, 20 and 21. The temperature of stream 19 will depend upon the solvent used, but will be low enough to avoid significant fouling from acrylic acid reaction. Stream 18 is cooled by indirect contact with stream 15 in exchanger 106 and, if necessary, by indirect contact with a cooling medium in exchanger 107, before being fed to the top of scrubber 102. Stream 20 is heated and partially or totally vaporized in heat exchanger 110, and the resulting vapor is returned to column 108. Stream 21, containing essentially all the acrylic acid produced in reactor 100, is sent to a separate unit for recovery or disposal of the acrylic acid.

The acrolein stripped in the lower section of column 108 enters the rectification section in which it is contacted with countercurrent reflux from streams 35 and 113. The product stream 22 is condensed primarily in heat exchanger 112. Uncondensed species pass to a second, lower-temperature condenser 113 in stream 23; thus all species but noncondensable gases are removed, and the remaining gases are routed to combustor 103.

The condensed acrolein product is passed to the acrolein derivative reactor via stream 24 without additional purification. The purity of stream 24 depends upon the solvent characteristics and the specific design and operation of the rectifying section. The acrolein composition in stream 24 typically would be between 88 and 97 weight percent acrolein. If desired, a vapor-phase acrolein stream could be fed to the acrolein derivative reactor simply by conducting a partial, rather than total condensation, in heat exchanger 112.

Stream 24 and the co-reactant feed stream 25 are fed to acrolein derivative reactor 115, the design of which may vary widely depending on the particular acrolein derivative being produced. Either feed stream may be a vapor or a liquid, as desired. The heat of the reaction is removed, or added as the case may be, in heat exchanger 116. The product stream 27 from reactor 115 comprises the desired acrolein derivative, typically with some residual unconverted reactants. Stream 27 may or may not require further processing, e.g., refining, before being withdrawn from the process.

EXAMPLES

The following examples are provided for illustrative purposes and are not intended to limit the scope of the claims which follow.

Example 1

In Example 1, acrolein and methyl mercaptan liquid feeds were vaporized and co-fed in a downward direction to a heated reactor tube which was 38 cm (14.9 in) long and 1.02 cm (0.40 in) in inside diameter. The reactor tube was filled with a solid packing which is identified in the example.

The product exiting the bottom of the reactor passed through a simple jacketed-tube condenser/cooler at 10° C. and was collected in a product vessel. Liquid-product samples for analysis were obtained with a syringe from the outlet of the condenser/cooler.

Example 1-A

Vapor-Phase MMP Reaction Over Stainless Steel Packing

The reactor tube was filled with 1/16-in size protruded stainless steel Pro-Pak® packing available from Chem-Pro Corporation, Fairfield, N.J.

Results of the runs are shown in the following table. Both runs were made at approximately 204 KPa (15 psig) reactor pressure. Concentrations of MMP and heavies, i.e., components exiting the gas chromatograph after MMP, are reported on a MeSH-and-acrolein-free basis.

TABLE 1

| Run | Rxtr Temp ° C. Top/ Bottom | MeSH Feed g/min | Acrolein Feed g/min | MeSH/ Acrolein Molar Ratio | MMP wt % | Heavies wt % |
| --- | --- | --- | --- | --- | --- | --- |
| 1 | 190/205 | 1.31 | 1.55 | 1.00 | 87.5 | 12.5 |
| 2 | 235/255 | 1.31 | 1.55 | 1.00 | 80.9 | 19.1 |

At both temperatures the predominant reaction product is MMP.

Example 1-B

Vapor-Phase MMP Reaction Over Stainless Steel Packing and Solid CaO Fragments

The first 28 cm of the reactor tube were filled with 1/16-in size protruded stainless steel Pro-Pak® packing. The remaining 10 cm of tube length were filled with 14–30 mesh fragments of a calcium oxide catalyst.

Results of the runs are shown in the following table. Both runs were made at approximately 204 KPa (15 psig) reactor pressure. Concentrations of MMP and heavies, components exiting the gas chromatograph after MMP, are reported on a MeSH-and-acrolein-free basis.

TABLE 2

| Run | Rxtr Temp ° C. Top/ Bottom | MeSH Feed g/min | Acrolein Feed g/min | MeSH/ Acrolein Molar Ratio | MMP wt % | Heavies wt % |
| --- | --- | --- | --- | --- | --- | --- |
| 1 | 186/206 | 1.30 | 1.54 | 1.00 | 84.4 | 15.6 |
| 2 | 225/254 | 1.31 | 1.54 | 1.01 | 86.8 | 13.2 |

As in the preceding example, the predominant reaction product is MMP at both run temperatures.

Example 2

This example shows the effect of utilizing propane to improve the efficiency of the reaction of propylene to acrolein. The experiments were carried out in a pilot-scale reactor system of two single reactor tubes of typical commercial dimensions. The first reactor tube contained a commercial propylene-to-acrolein catalyst which is comprised of bismuth, molybdenum, and iron oxides and other promoters. The second stage, which was close-coupled to the first, contained a commercial acrolein-to-acrylic acid catalyst comprised of bismuth, molybdenum, and iron oxides and other promoters. The second stage was used as an effective means of converting acrolein for disposal. Each stage had a jacket of a heat transfer fluid to remove heat of reaction. Thermocouples were placed strategically to measure hot spots in each system. The gaseous reactants were introduced via gas mass flow meters. The pressure at the entrance of the first stage was held at a constant 28 psig. The final product out of the second stage was passed through a scrubber and then condensed to equilibrium at 4° C., leaving only noncondensables. Concentration measurements of the feed, first-stage effluent, second-stage effluent, and the recycle stream were obtained via a gas chromatograph. Fresh propylene feed concentration was held at 8.2 mole percent and the gas hourly space velocity held at 1800 hr$^{-1}$.

Example 2-A

A baseline experiment was run with a 303° C. jacket temperature, 12.1 mole percent feed oxygen concentration, 49.3 mole percent feed nitrogen concentration, 30.0 mole percent steam concentration, and 0.3 mole percent feed propane concentration. Overall, the process was once-through only with no recycle. In the first stage, 90.5 percent of the feed propylene was consumed by the reaction. Of the propylene consumed, 79.9 percent went directly to forming acrolein in the first-stage outlet. Overall, 72.3 percent of the propylene fed to the system ends up as the useful product acrolein, while the rest is essentially lost. To make 3.8 standard liters per minute ("slm") of acrolein, 5.3 slm of propylene are required. This experiment is representative of typical commercial operation.

Example 2-B

In comparison, a recycle process was run with a high concentration of propane at similar conditions of active ingredients. The experiment was run with a jacket temperature of 303° C., 14.1 mole percent feed oxygen concentration, 8.7 mole percent feed water concentration, and 6.2 mole percent propane concentration. Essentially no nitrogen was in the feed. 98–99 percent of the second-stage noncondensable gases were returned to feed of the first stage to maintain constant pressure levels. In the first stage, 90.6 percent of the feed propylene was consumed by reaction. Of the propylene consumed, 87.6 percent went directly to forming acrolein in the first-stage outlet. Overall, 79.4 percent of the propylene fed to the system ends up as acrolein. To make 3.8 slm of acrolein, 4.8 slm of propylene is required. The experiment requires only 91 percent of the propylene required for once-through operation.

The improvement in propylene utilization arises from two factors. The first is the nearly complete recycling of unreacted material back to the front of the reactor. This accounts for 60 percent of the decrease in propylene requirements. The second factor is the presence of the relatively high concentration of propane in the feed. This increased concentration increases the flowing heat capacity and reduced temperatures in the system considerably. Overall, this effect accounts for 40 percent of the observed improvement in propylene usage.

Propane is introduced to the process as an impurity in the propylene feed. The propane levels of this experiment are consistent with 1–2 mole percent impurity level. Recycle operation makes economically viable the use of lower-purity propylene which can be more cost effective.

Example 3

Reaction of Acrolein with Butadiene 5.6 pounds per hour of liquid acrolein prepared according to Example 2-B is mixed with 5.4 pounds per hour of butadiene and 17 pounds per hour of an inert hydrocarbon solvent such as hexane, heptane, or cyclohexane. The resulting reaction mixture is compressed to about 600–700 psig and fed to a carbon steel tubular reactor at about 150–160° C. The reactor effluent containing 5.5 pounds per hour of tetrahydrobenzaldehyde (THBA), 2.8 pounds per hour of acrolein, 2.7 pounds per hour of butadiene, 17.0 pounds per hour of inert solvent, and the water and acetaldehyde contained in the acrolein feed is fed to a stripper where the acrolein, butadiene, water, acetaldehyde and inert solvent are taken overhead and condensed. The condensed overhead is fed to a decanter where the water and water soluble acetaldehyde are separated from the acrolein, butadiene, and inert solvent. The acrolein, butadiene and inert solvent are recycled to the reactor and the water containing acetaldehyde is removed from the process. The tails from the stripper containing crude THBA is further refined to produce 99.8% or higher purity THBA. Typical acrolein and butadiene efficiencies to THBA are greater than 90%.

Example 4

Reaction of Acrolein with Substituted Butadiene 96 grams of acrolein prepared according to Example 2-B are fed to a glass batch reactor containing 230 grams of 2-(4-hydroxy-4-methylpentyl)-butadiene which is heated to 60° C. After the acrolein addition is complete, the reaction mixture is heated to 90° C. and about 20 grams of water is added. Then the pressure is reduced to about 300 mm Hg. Unreacted acrolein, water and acetaldehyde are stripped overhead and collected for disposal. The crude reaction mixture contains 4-(4-hydroxy-4-methylpentyl)-3- cyclohexene-1-carboxaldehyde, a product useful as a fragrance. Acrolein and myrcenol efficiencies to Lyral are greater than 90%.

Example 5

Reaction of Acrolein with a Vinyl Ether 5.6 pounds per hour of liquid acrolein prepared according to Example 2-B is mixed with 22.4 pounds per hour of vinyl methyl ether and the resulting reaction mixture is compressed to about 600–700 psig and fed to a metal tubular reactor at about 170–175° C. The reactor effluent containing 5.7 pounds per hour of 2-methoxy-3,4-dihydro-2H-pyran ("MDP"), 19.5 pounds per hour of vinyl methyl ether, 2.8 pounds per hour of unreacted acrolein, and the water and acetaldehyde originally contained in the acrolein feed is fed to a stripper where the acrolein, vinyl methyl ether, water, and are taken overhead and condensed. The condensed overhead is fed to a decanter where additional water is added and the water soluble acetaldehyde is separated from the acrolein and vinyl methyl ether. The acrolein and vinyl methyl ether are recycled to the reactor and the water containing acetaldehyde is removed from the process. The tails from the stripper containing crude MDP is further refined to produce 99.9% or higher purity product, suitable for use as the raw material for glutaraldehyde manufacture. Typical acrolein and vinyl methyl ether efficiencies to MDP are greater than 95%.

Example 6

Production of Glutaraldehyde from MDP 114 grams of MDP produced as described in Example 5 is mixed with an equal amount of water acidified to pH 2.0–2.5 and the resulting mixture is stirred under an inert atmosphere and heated to 85–95° C. to produce glutaraldehyde and methanol. The methanol is removed from the glutaraldehyde by distillation under reduced pressure and the pH of the product is adjusted to 3.5–4.0 by addition of a weak base. The resulting aqueous glutaraldehyde is suitable for use as a biocide. The efficiency of MDP to glutaraldehyde is greater than 90%.

Example 7

Dimerization of Acrolein 5.6 pounds per hour of acrolein prepared according to Example 2-B is mixed with 22.4 pounds per hour of an inert, hydrocarbon solvent such as hexane, heptane or cyclohexane and fed to a metal tubular reactor at about 600 psig and 190° C. The reactor effluent containing 2.7 pounds per hour of 2-formyl-3,4-dihydro-2H-pyran ("acrolein dimer"), 2.8 pounds per hour of acrolein, 22.4 pounds per hour of inert solvent and the water and acetaldehyde originally contained in the acrolein feed is fed to a stripper where the acrolein, water, inert solvent, and acetaldehyde are taken overhead and condensed. The condensed overhead is fed to a decanter where additional water is added and the water soluble acetaldehyde is separated from the acrolein and inert solvent. The acrolein and inert solvent are recycled to the reactor and the water containing acetaldehyde is removed from the process. The tails from the stripper containing crude acrolein dimer is further refined to produce 98% or higher purity product. Typical acrolein efficiency to acrolein dimer is greater than 90%.

Example 8

Addition of Alcohols to the Acrolein Carbon-Carbon Double Bond 100 grams of acrolein prepared according to Example 2-B is added to 114 grams of methanol containing 1 wt % triethyl amine at 10 to 20° C. After the acrolein addition, the triethyl amine catalyst is neutralized by addition of a weak organic acid and the unreacted acrolein and methanol and water and acetaldehyde contained in the acrolein feed are removed by distillation under reduced pressure. The crude 3-methoxypropionaldehyde is purified by distillation under reduced pressure to give 143 grams of greater than 98% pure product.

Example 9

Addition of Alcohols to the Acrolein Carbon-Oxygen Double Bond 400 grams of acrolein prepared according to Example 2-B is added to 320 grams of commercial grade pentaerythritol in a 1-liter glass round-bottomed flask. Then, 0.7 grams of para-toluene sulfonic acid catalyst is added and the resulting slurry is stirred and heated to 55–60° C. for about three hours. Then the catalyst is neutralized by addition of a weak base and the excess acrolein, water of reaction, and acetaldehyde is removed by distillation at about 80–90 mm Hg. When the reactor temperature reaches about 60° C., the pressure is reduced to about 3 mm Hg and the product 3,9-divinylspirobi(m-dioxane) is collected overheat. Altogether, 300 grams of 98% pure product is obtained, representing a 61% yield based on pentaerythritol.

Example 10

Addition of Alcohols to the Acrolein Carbon-Carbon Double Bond and the Acrolein Carbob-Oxygen Double Bond 100 grams of acrolein prepared according to Example 2-B is added to 418 grams of allyl alcohol containing 0.1 wt % para-toluene sulfonic acid. The reaction mixture is heated to 55–60° C. for 2 hours and then the acid catalyst is neutralized by addition of weak base and the unreacted acrolein and allyl alcohol along with water and acetaldehyde are removed by distillation under reduced pressure. The product 1,1,3-tri (allyloxy)propane, is purified by distillation at reduced pressure to give 370 grams of 98% pure product. The efficiency of acrolein to tri(allyloxy)propane is 90%.

Example 11

Addition of water to Acrolein 100 grams of acrolein prepared according to Example 2-B is added to 500 grams of water containing 10 grams of a solid acidic catalyst such as an acidic zeolite. The mixture is stirred at 60° C. for 4 hours and then is filtered to remove the solid catalyst. The aqueous solution is distilled at reduced pressure to remove unreacted acrolein, a portion of the water, and the acetaldehyde. The distillate is condensed and the aqueous layer containing the acetaldehyde separated and the acrolein recovered for subsequent reaction. The stripped product contains 105 grams of 3-hydroxypropion-aldehyde in 450 grams water. The yield of 3-hydroxypropionaldehyde from acrolein is 80% and the product is suitable for use as raw material in the production of 1,3-propanediol.

Example 12

Production of 1,3-propanediol from 3-hydroxypropionaldehyde

The aqueous solution of 3-hydroxypropionaldehyde prepared in Example 11 is treated with hydrogen at 200 psig and 50° C. in the presence of 5 weight % Raney Nickel to give 107 grams of 1,3-propanediol. After the reaction, the Raney Nickel catalyst is separated from the aqueous product by filtration. The yield of 1,3-propanediol based on 3-hydroxypropionaldehyde is 99%.

Although the invention has been described with respect to specific aspects, those skilled in the art will recognize that other aspects are intended to be within the scope of the claims that follow.

What is claimed is:

1. A process for producing acrolein comprising:
   (i) passing a propylene feedstream comprising propylene, oxygen and a recycle gas comprising propane, oxygen and at least one of carbon monoxide or carbon dioxide to an acrolein reaction zone wherein the propylene feedstream is contacted with an acrolein reaction catalyst at conditions effective to promote the formation of acrolein to provide an acrolein effluent stream comprising acrolein, propane, acetaldehyde and water;
   (ii) passing the acrolein effluent stream to an acrolein separation zone wherein the acrolein effluent stream is partially condensed to provide a liquid acrolein product stream comprising acrolein, acetaldehyde and water and a recycle gas stream comprising the recycle gas;
   (iii) recycling at least a portion of the recycle gas stream to the acrolein reaction zone:
   characterized in that the propylene feedstream comprises an amount of propane of from about 5 to 70 volume percent and effective to provide a propylene-to-acrolein reaction efficiency of from about 75 to 90 mole percent.

2. The process of claim 1 wherein the acrolein product stream comprises from about 0.5 to 3.5 weight percent acetaldehyde.

3. The process of claim 1 wherein the acrolein product stream comprises from about 88 to 97 weight percent acrolein.

4. The process of claim 1 further comprising:
   (a) passing a propane feedstream comprising at least 30 mole percent propane, oxygen and the recycle gas comprising propane, oxygen and at least one of carbon monoxide or carbon dioxide to a propylene reaction zone at conditions to promote the formation of propylene to provide a preliminary oxidation effluent stream comprising propylene and propane; and
   (b) passing the preliminary oxidation effluent stream to the acrolein reaction zone to comprise at least a portion of the propylene feedstream.

5. The process of claim 4 comprising combining at least a portion of the recycle gas stream with propane and oxygen to form the propane feedstream.

* * * * *